United States Patent

Humphrey et al.

[11] Patent Number: 5,992,000
[45] Date of Patent: Nov. 30, 1999

[54] STENT CRIMPER

[75] Inventors: John W. Humphrey, Eden Prairie; Terry V. Brown, Fridley; Charles L. Euteneuer, St. Michael; Nam H. Hoang, Minneapolis; Leo M. Klisch, Maple Grove; Christopher R. Larson, St. Paul; Jonathan C. Sell, West St. Paul, all of Minn.; Vladimir B. Tsukernik, West Roxbury, Mass.; Lawrence W. Ulanowski, Brooklyn Park, Minn.

[73] Assignee: SciMed Life Systems, Inc., Maple Grove, Minn.

[21] Appl. No.: 08/951,550

[22] Filed: Oct. 16, 1997

[51] Int. Cl.⁶ .................................................. B21D 39/00
[52] U.S. Cl. ............................. 29/516; 29/282; 29/283.5
[58] Field of Search ........................... 29/282, 423, 516, 29/517, 234, 235, 283, 283.5; 606/1, 108, 198; 623/1

[56] References Cited

U.S. PATENT DOCUMENTS

| | | |
|---|---|---|
| 5,026,377 | 6/1991 | Burton et al. ............................ 606/108 |
| 5,183,085 | 2/1993 | Timmermans ............................ 140/89 |
| 5,290,305 | 3/1994 | Inoue ....................................... 606/191 |
| 5,338,295 | 8/1994 | Conrelius et al. ........................ 604/96 |
| 5,437,083 | 8/1995 | Williams et al. ......................... 29/235 |
| 5,509,184 | 4/1996 | Herrero .................................... 29/282 |
| 5,546,646 | 8/1996 | Williams et al. ......................... 29/407 |
| 5,591,222 | 1/1997 | Susawa et al. ............................ 623/1 |
| 5,626,604 | 5/1997 | Cottone, Jr. .............................. 606/198 |
| 5,628,754 | 5/1997 | Shevlin et al. ........................... 606/108 |
| 5,630,830 | 5/1997 | Verbeek ................................... 606/198 |
| 5,672,169 | 9/1997 | Verbeek ................................... 606/1 |
| 5,700,285 | 12/1997 | Myers et al. ............................. 623/1 |
| 5,725,519 | 3/1998 | Penner et al. ............................ 606/1 |
| 5,736,251 | 4/1998 | Pinchuck ................................. 606/1 |
| 5,738,674 | 4/1998 | Williams et al. ......................... 606/1 |
| 5,746,764 | 5/1998 | Green et al. ............................. 606/194 |
| 5,749,921 | 5/1998 | Lenker et al. ............................ 623/1 |
| 5,766,203 | 6/1998 | Imran et al. ............................. 606/198 |
| 5,810,871 | 9/1998 | Tuckey et al. ........................... 606/198 |
| 5,810,873 | 9/1998 | Morales .................................. 606/198 |
| 5,836,952 | 11/1998 | Davis ...................................... 606/108 |
| 5,860,966 | 1/1999 | Tower ..................................... 606/1 |
| 5,893,852 | 4/1999 | Morales . |
| 5,893,867 | 4/1999 | Bagaoisan et al. . |

FOREIGN PATENT DOCUMENTS

| | | |
|---|---|---|
| 0 630 623 A2 | 12/1994 | European Pat. Off. . |
| 0 701 800 | 3/1996 | European Pat. Off. . |
| 295 06 654 | 7/1995 | Germany ...................... A61M 29/00 |
| 195 32 288 A1 | 3/1997 | Germany ...................... A61M 29/00 |
| WO 96/03092 A1 | 2/1996 | WIPO .............................. A61F 2/02 |
| WO 97/20593 | 9/1997 | WIPO .............................. A61M 29/00 |
| WO 98/19633 | 5/1998 | WIPO .............................. A61F 2/06 |

OTHER PUBLICATIONS

Derwent Abstract Accession No. 93–135787/199317, abstract of DE 4235004, 1993.

*Primary Examiner*—S. Thomas Hughes
*Assistant Examiner*—Jermie E. Cozart
*Attorney, Agent, or Firm*—Vidas, Arrett & Steinkraus

[57] ABSTRACT

An apparatus for crimping a stent to a catheter as well as a method for crimping a stent to a catheter are disclosed in several embodiments. The apparatus in its various embodiments involves the application of a uniform radially inward force to a compressible tube in which the stent and catheter are situated.

21 Claims, 9 Drawing Sheets

STENT CRIMPER

BACKGROUND OF THE INVENTION

This invention relates to an assembly and a method for fastening a stent onto a catheter. This kind of device finds routine use in the area of percutaneous transluminal coronary angioplasty (PTCA) procedures, although it may be used in other types of procedures, as well.

Stents and stent delivery assemblies are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Inflation expandable stents are well known and widely available in a variety of designs and configurations. Inflation expandable stents are crimped to their reduced diameter about the delivery catheter, then maneuvered to the deployment site and expanded to the vessel diameter by fluid inflation of a balloon positioned between the stent and the delivery catheter. The present invention is particularly concerned with the crimping of inflation expandable stents although self-expanding stent may be used as well.

An example is the stent described in PCT Application NO. 960 3092 A1, published Feb. 8, 1996, the content of which is incorporated herein by reference.

In advancing an inflation expandable balloon through a body vessel to the deployment site, the stent must be able to securely maintain its axial position on the delivery catheter, without translocating proximally or distally, and especially without becoming separated from the catheter. Stents that are not properly secured or retained to the catheter may slip and either be lost or be deployed in the wrong location. The stent must be crimped in such a way as to minimize or prevent altogether distortion of the stent and to thereby prevent abrasion and/or reduce trauma of the vessel walls.

In the past, this crimping has been done by hand resulting in non-uniform crimps due to the application of uneven force to the stent. A non-uniformly crimped stent must either be discarded or re-crimped. Stents which have been crimped multiple times can suffer from fatigue. Moreover, a non-uniform crimping can result in scoring or other marking of the stent which can cause thrombosis. A poorly crimped stent can also damage the underlying balloon. Other methods of crimping stents include the use of mechanical devices such as those disclosed in U.S. Pat. No. 5,546,646 to Williams et al, U.S. Pat. No. 5,183,085 to Timmermans et al., U.S. Pat. No. 5,626,604 to Cottone, Jr. and WO 97/20593.

It is a goal of the present invention to produce a device, optionally portable, to crimp a stent onto a catheter uniformly while minimizing the distortion of and scoring and marking of the stent and due to the crimping. This goal is accomplished in the present invention in its many embodiments by applying a uniform force to a compressible tube in which the stent and catheter are situated.

In the description that follows it is understood that the invention contemplates crimping a stent to a catheter with an expandable region. Thus, when reference is made to crimping a stent to a catheter, a balloon may be situated between the stent and the catheter,or the stent may be crimped to a region of a catheter having some other means for expanding.

SUMMARY OF THE INVENTION

The present invention provides an apparatus for compressing a stent onto a catheter, the catheter preferably including are expandable portions such as a balloon under the stent. The apparatus comprises a retaining means for preventing the stent from sliding along the catheter and a crimping means for applying a substantially uniform, circumferential radial inward force to at least a portion of the stent. The crimping means moves longitudinally with respect to the stent and over it to apply a substantially uniform circumferential radial inward crimping force to the stent.

In one embodiment, the retaining means comprises a peel away tube mounted coaxially on the catheter adjacent to the proximal of the stent. In another embodiment, the retaining means comprises deformable tubing mounted coaxially on the catheter over the stent. The deformable tubing has a first diameter prior to stretching and a second smaller diameter after stretching. The deformable tubing grips the uncrimped stent and holds it in place upon being stretched.

In another embodiment, the crimping means comprises a tapered peel away tube mounted coaxially on the catheter adjacent to the distal end of the stent. The tapered peel away tube has a first diameter larger than the diameter of the stent and a second diameter smaller than the diameter of the uncrimped stent. The uniform circumferential radial inward force is applied by sliding the tapered peel away tube over the stent.

In another embodiment, the crimping means comprises a die having a bore. The diameter of the bore is smaller than the diameter of the stent. The uniform radial inward force is applied by introducing the stent into the bore and sliding the die over the stent.

The present invention in another embodiment provides an apparatus for compressing a stent comprising a tube having a first end and a second end, the tube preferably having a longitudinal axis coincident with the longitudinal axis of the apparatus, the tube characterized by a first diameter in the absence of tension and a second smaller diameter when longitudinal tension is provided on the tube, the tube receiving a catheter and a stent to be crimped to said catheter, said stent having an initial diameter prior to being crimped and a final diameter after being crimped and a die having a bore sized to crimp the stent, the longitudinal axis of the bore coincident with the longitudinal axis of the tube, the tube at least partially resting within the bore of the die. The stent is crimped to the catheter with the above device by providing tension to the tube thereby reducing its diameter and causing it to grip the stent and sliding the die along the tube and over the stent. The invention further comprises a slide means to which the die is mounted to facilitate sliding the die over the stent.

In another embodiment of the invention, an apparatus for compressing a stent is disclosed comprising a deformable tube and tension applying means for applying longitudinal tension to the deformable tube. The deformable tube, fastened to the tension applying means is characterized by a first diameter in the absence of tension and a second smaller diameter when longitudinal tension is provided on the tube. A stent is crimped onto a catheter using the above-described apparatus by applying longitudinal tension via the tension applying means to the deformable tube whereby the diameter of the deformable tube decreases as the tube is stretched, thereby crimping the stent.

In another embodiment, the present invention is directed to a method of crimping a stent onto a catheter. The method comprises placing a stent coaxially on stent bearing region of the catheter, placing a stent retaining means on the catheter, applying a stent crimping means, the means being capable of applying a uniform radial inward force to at least a portion of the stent, to the stent and removing the stent crimping means and stent retaining means. The stent retention means may comprises a peel away tube mounted adjacent to the stent or may comprise a deformable tube, the diameter of the tube reducing on stretching, which is placed over the stent and stretched. The stent crimping means may comprise a tapered tube slidably mounted coaxially over the catheter, the tube having first and second ends, the first end having a larger diameter than the stent and the second end having a smaller diameter than the stent. In use, the stent crimping means is applied by sliding it over the stent.

In yet another embodiment, the present invention is directed to a method for affixing a stent onto a catheter. The method involves placing a stent coaxially on the stent bearing region of the catheter and optionally placing a peel away tube coaxially on the stent bearing region of the catheter. The first end of a tapered, optionally peel-away sheath having first and second ends, the first end having a larger diameter than the second end, is placed coaxially over a part of the peel away tube. The peel-away tube and stent and catheter therein is slidably moved through the tapered peel away sheath until the stent is crimped onto the catheter. Thereafter, the peel-away sheath is peeled away, as is the optional peel-away tube.

In yet another embodiment, the present invention is directed to an apparatus for crimping a stent comprising a catheter, the catheter having a stent bearing region and a stent mounted thereon and, optionally, a balloon mounted at least partially underneath the stent. The apparatus further comprises a peel away tube mounted coaxially on the catheter adjacent to one end of the stent, the peel away tube serving as a stop to prevent sliding of the stent during crimping. The apparatus further comprises a tapered peel away tube surrounding the catheter at the second end of the stent. The diameter of the first end of the tapered peel away tube exceeds the diameter of the uncrimped stent while the diameter of the second end of the tapered peel away tube is less than the diameter of the uncrimped stent.

In yet another embodiment, the present invention is directed to an apparatus for crimping a stent comprising a tubular plunger having a first end and a second end, the plunger having an inner diameter exceeding the diameter of the stent prior to crimping, a deformable inner tube for receiving the stent and catheter from the plunger, the inner tube fixedly attached to the second end of the tubular plunger, the deformable inner tube having a first end and a second end, an outer tube, the outer tube having a first and a second end, the outer tube notched at the second end so as to have a plurality of oppositely situated wall sections at the second end, the second end of the plunger slidably mounted in the first end of the outer tube and the deformable inner tube residing within the outer tube, a die slidably mounted on the outer tube, the die comprising an outer housing and an inner housing, the outer housing in communication with the inner housing, the inner housing having an inner bore therethrough, the inner bore having a circular cross-section at every point along the length of the inner bore, the bore characterized by a minimum diameter, the diameter of the stent prior to crimping exceeding the minimum diameter of the bore, a portion of the inner tube traversing the bore, the die further having one or more slots therethrough between the inner housing and the outer housing, the slots arranged so as to receive the plurality of oppositely situated wall sections in sliding engagement and an end portion, the end portion residing at the second end of the outer tube, the end portion optionally having a hole therein from which the catheter may emanate. The stent is crimped to the catheter by inserting the stent and catheter through the plunger and into the inner tube, and sliding the die along the outer tube such that the die passes over the stent and applies a uniform radial inward force to the stent.

BRIEF DESCRIPTION OF THE FIGURES

FIGS. 10b and 10c show a side view of a stent in the process of being crimped in the stent crimper depicted in FIG. 10a;

DETAILED DESCRIPTION OF THE INVENTION

Figure 1:
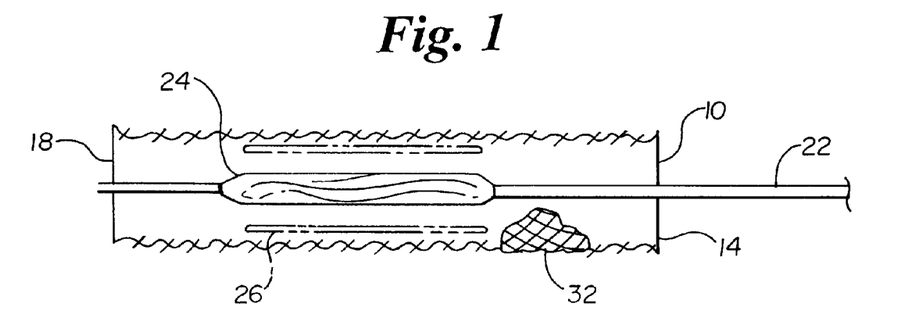
FIG. 1 shows a side view of one embodiment of the present invention.

The present invention provides an apparatus for compressing a stent onto a catheter. In a preferred embodiment the catheter includes an expansive means, such as a balloon over which the stent is crimped. The apparatus comprises a retaining means for preventing the stent from sliding along the catheter and a crimping means for applying a substantially uniform, circumferential radial inward force to at least a portion of the stent. The crimping means moves longitudinally with respect to the stent and catheter As shown in FIG. 1, all embodiments of the apparatus for crimping a stent include an optional tube 10 having a first end 14 and a second end 18. The tube may serve as a retaining means to prevent the stent from sliding along the catheter. Tube 10 is characterized by a first diameter in the absence of tension and a second smaller diameter when longitudinal tension is provided on the tube. While the interior of the tube has a round cross-section, the exterior need not be round. Optionally, tube 10 has a longitudinal axis coincident with the longitudinal axis of the apparatus. Tube 10 receives a catheter 22 (shown with a balloon 24 thereon) and a stent 26 over the catheter and balloons to be crimped to said catheter, the stent having an initial diameter prior to being crimped and a final smaller diameter after being crimped. The tube also helps to prevent or minimize the elongation of the stent during the crimping process and protects the stent.

Tube 10 may comprise any material that exhibits a reduced diameter upon the application of tension thereto and that has a relatively smooth interior surface to avoid marking, scoring or otherwise damaging the stent. The tube may be made of any material that is softer than the die used to crimp the stent, that won't stick to the stent and that won't damage the stent, including polymers. One such material is polyester. However, materials such as teflon, polyethylene, polyurethane and nylon may also be used. Additionally, the tube, having an interior surface and an exterior surface, may be made of a lubricious material or have a lubricious coating thereon. One surface of the tube may be more lubricious than the other. Preferably, the tube will be transparent or translucent so as to facilitate the viewing of the stent position therein. The tube must be round on the inside, but need be round on the outside.

Figure 2:
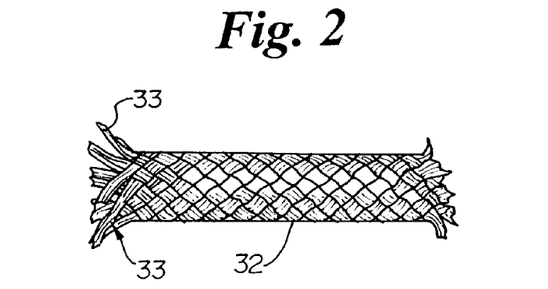
FIG. 2 shows a side view of a braid element used in the invention.

The tube may comprise a polymer braid as illustrated at 32 and in FIG. 2. Individual strands 33 of a given polymer are interwoven as shown in FIG. 2 to form tubular braid 32. The polymer strands must be thick enough to provide structural integrity to the tube but not so thick as to prevent elongation of the tube and the associated constriction upon elongation. Moreover, the weave must be dense enough as to prevent parts of the stent, depending on the design of the stent, from penetrating the weave and becoming enmeshed in it. In a preferred embodiment, individual strands 33 made of polyester having a circular cross section of diameter 5/1000 inch. Strands 32 are woven together in a clothing weave to form tubular braid 32 with the weave being about 20 to about 90 picks/inch, desirably about 32 picks/inch. The braid tube described is manufactured by SCIMED Life Systems, Inc., Maple Grove, Minn. and/or SantaFe Textiles, Inc., Los Angeles, Calif., or may be manufactured by any other coil braider.

Figure 3:
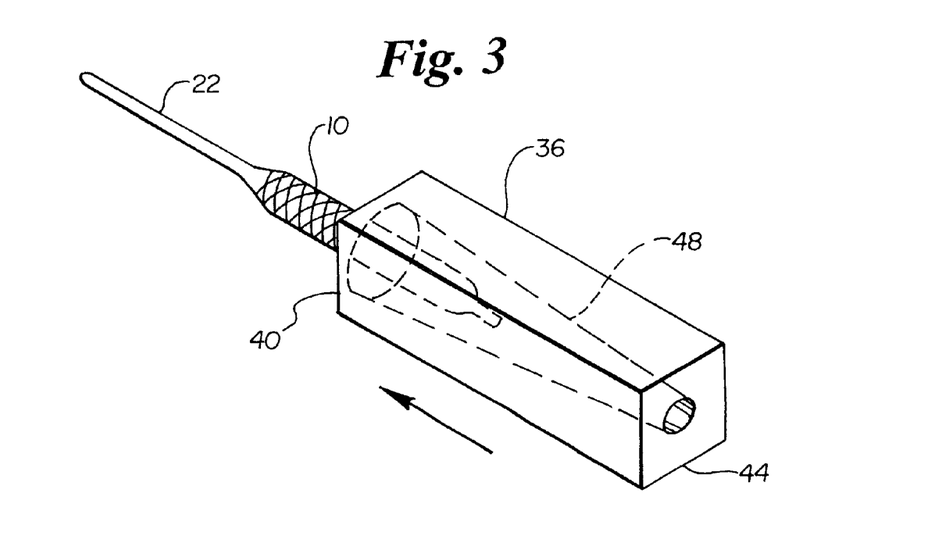
FIG. 3 show a perspective view of a die moving over a stent or a catheter.

One embodiment of the present invention, as illustrated in FIG. 3, comprises a crimping means consisting of a die 36 having a first end 40, a second end 44 and a bore 48 within. The longitudinal axis of the bore is coincident with the longitudinal axis of the cathater 22. The bore is sized to crimp a stent carried on catheter 22 within tube 10 to its mounted diameter which is smaller than the initial diameter of the stent. Tube 10 as shown partially rests within bore 48 of die 36. The stent, located underneath tube 10 and not depicted in the FIG. 3, is crimped to the catheter by providing tension to tube 10 thereby reducing its diameter and causing it to grip the stent and by sliding die 36 along tube 10 and catheter 22, over the stent and tube. As depicted in FIG. 3, the bore may optionally be tapered at the second end 44, the diameter of the bore at the second end of the die 44 having a diameter smaller than the initial diameter of the stent i.e. the desired crimped diameter. Alternatively, the bore may be tapered inward from both ends. Thus, the diameter of the bore at the first end of the tube and at the second end of the tube will be greater than the diameter of the bore in the middle of the tube. Die 36 may be made of any material that is harder or less deformable than the stent to be crimped including metals such as stainless steel and polymers such as polycarbonate, acrylonitrile-butadiene-styrene copolymer, Nylon, acetal, and PEEK (polyetheretherketone).

Tube 10 may further comprise a lubricious coating on the exterior surface to facilitate the sliding movement of die 36 over tube 10 or on the interior surface to facilitate insertion of catheter 22 and stent 26 therein. Suitable lubricious coatings include, but are not limited to, silicone and hydrophillic coatings involving hydrogel polymers or the like, such as polymer networks of a vinyl polymer and an uncrosslinked hydrogel, for example. Polyethylene oxide (PEO) is a preferred hydrogel. A preferred vinyl polymer is neopentyl glycol diacrylate (NPG). Other compositions include copolymers of poly(ethylene-maleic anhydride). Such compositions are more fully disclosed in copending U.S. patent application "Lubricity Gradient for Medical Devices", Ser. No. 08/868301, filed Jun. 3, 1997, and in copending U.S. patent application Ser. No. 08/409797 filed Mar. 24, 1995, both of which are assigned to the same assignee as is the present invention and which are incorporated herein by reference as well.

The apparatus may further comprise a die sliding device to facilitate sliding the die over the stent. The die sliding device provides a track along which the die may be slidably moved. The die sliding device may be made of metals such as stainless steel and polymers such as polycarbonate, acrylonitrile-butadiene-styrene copolymer and PEEK (polyether ether ketone).

Figure 4:
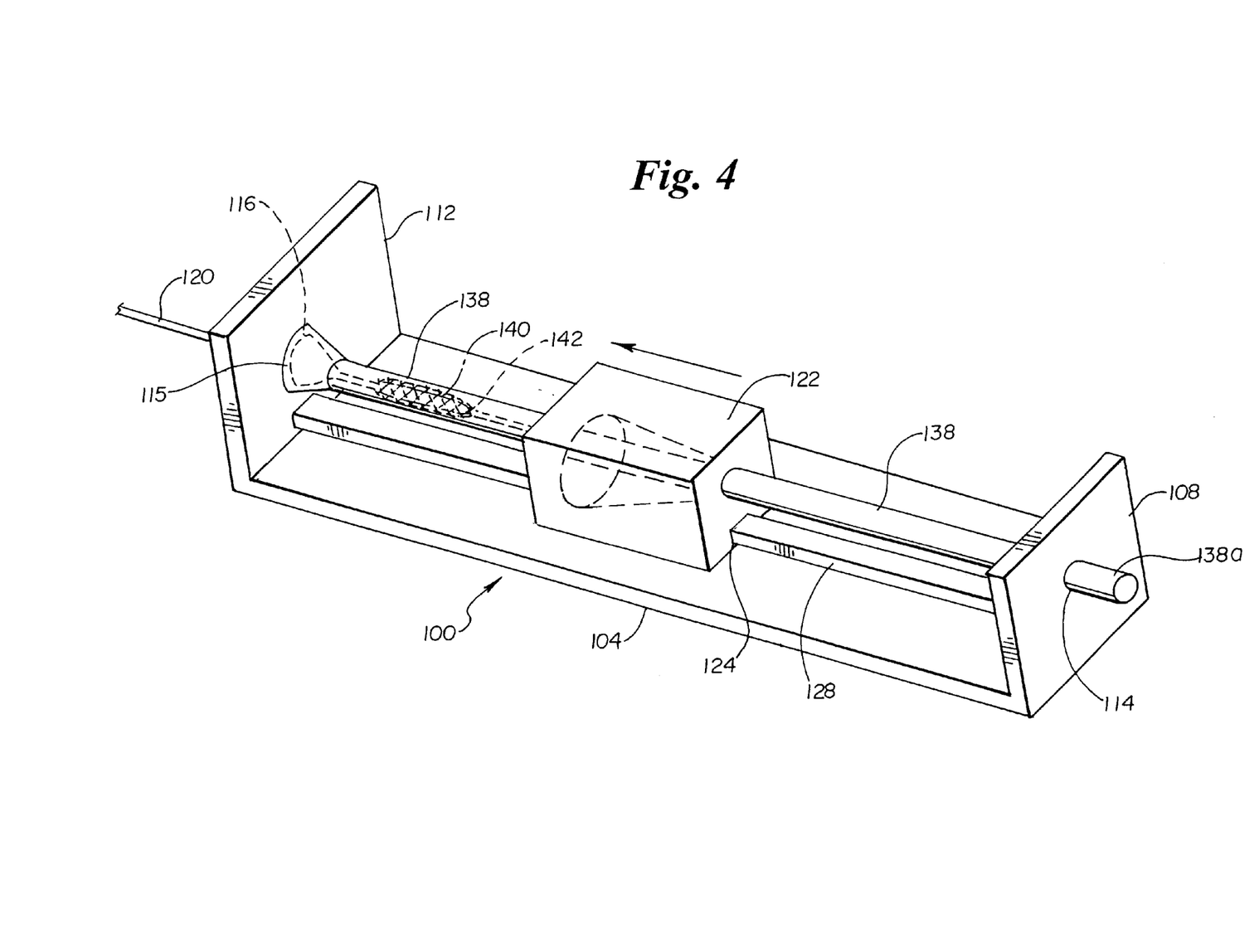
FIG. 4 shows a perspective view of another embodiment of the present invention including a mounting apparatus.

In one embodiment, illustrated in FIG. 4, a die sliding device generally designated at 100 consists of a base 104 with two vertical oriented end members 108 and 112 emanating therefrom. Vertical end 108 has aperture 114 formed therein, while vertical end 112 has a male conical protrusion 115 therefrom with an aperture 116 formed therein. The diameter of aperture 116 is large enough to accommodate the largest diameter catheter 120 desired to be used with the present invention. A die 122 has an elongated groove 124 formed on its bottom and is slidably mounted by means of groove 124 on a track 128. An inner tube 138 is attached either adhesively or by pressing to male protrusion 115 at end member 112 and extends through aperture 114 at the other end member 108. In use, catheter 120 is inserted through aperture 116 into inner tube 138. Stent 140 is placed over the expandable stent bearing portion of the catheter 142. Inner tube 138 is placed under tension by pulling on end 138a causing the inner tube to grip stent 140 and hold it in place over the expandable stent bearing region of catheter 142. Die 122 is then slidably moved along the track 128 and over expandable stent bearing region of the catheter 142 as indicated by the arrow until stent 140 is crimped. Catheter 120 may then be removed after slidably moving die 122 back over the stent to its initial position as shown in the Figure. Of course stent 140 and expandable stent bearing region of catheter 142 must be inserted far enough into inner tube 138 to allow the die to pass over them.

Figure 5:
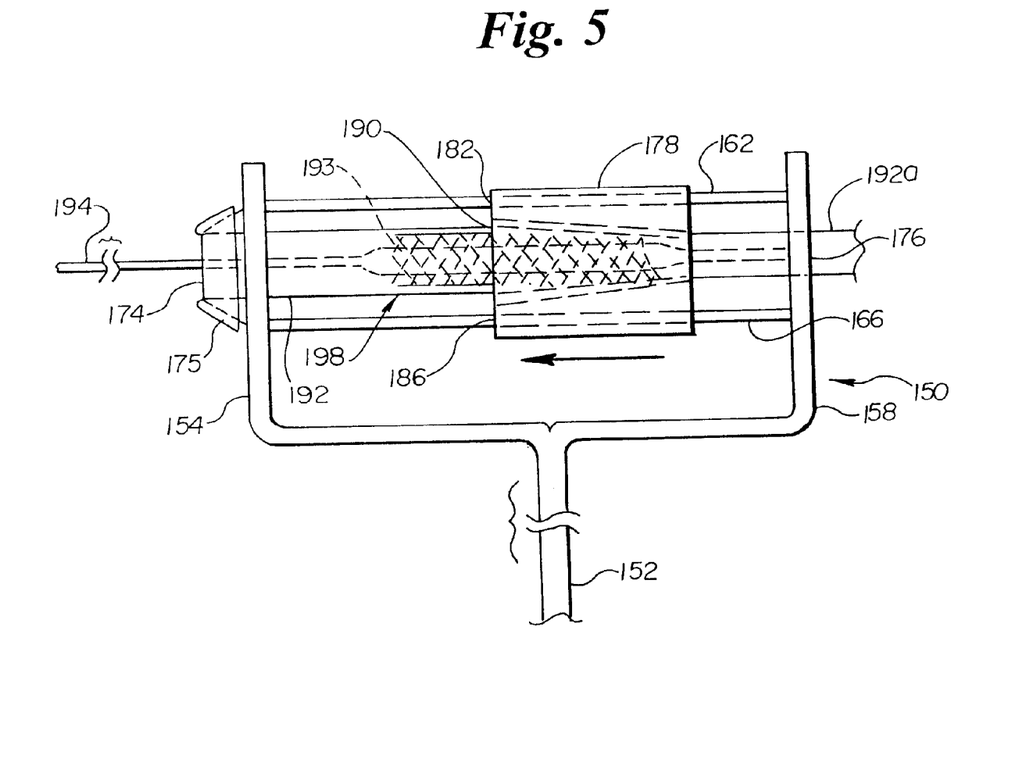
FIG. 5 shows a side view of another embodiment of the present invention including a mounting apparatus.

In another embodiment, illustrated in FIG. 5, a Y or similar shaped frame generally indicated at 150 having a handle 152 and uprights 154 and 158, has two rods 162 and 166 mounted between uprights 154 and 158. A tubular or conical protrusion 175 with an aperture 174 therethrough extends out from upright 154. Aperture 174 extends through upright 154. A second aperture 176 extends through upright 158. A die 178, having three bores 182, 186 and 190 is slidably mounted on the rods 162 and 166 by means of bored 182 and 186, respectively. Rod 162 traverses bore 182 while rod 166 traverses bore 186. An inner tube 192 die extending outwardly through aperture 174 folded back over and fastened to protrusion 175 at one end, extends through die 178 and bore 190 therein and out through aperture 176 in upright 158. Inner tube 192 may be adhesively bonded to the protrusion or pressed on. Alternatively, protrusion 175 may be threaded (not shown) and a threaded collar (not shown) screwed on, with the folded back portion of inner tube 192 wedged between the collar and protrusion 175. In use, catheter 194 is inserted in inner tube 192 through aperture 174 in upright 154, and at least partially into bore 190 in die 178. Stent 193 is carried on the catheter over the stent bearing region of the catheter indicated generally at 198. Tension is applied to inner tube 192 by pulling on the end 192a emanating from aperture 176 thereby gripping stent 193 and holding it in place over the stent bearing region of the catheter at 198. Die 178 is slidably moved along rods 182 and 186 as indicated by the arrow such that stent bearing region 198 of catheter 194 passes through bore 190 thereby crimping the stent.

Figure 6:
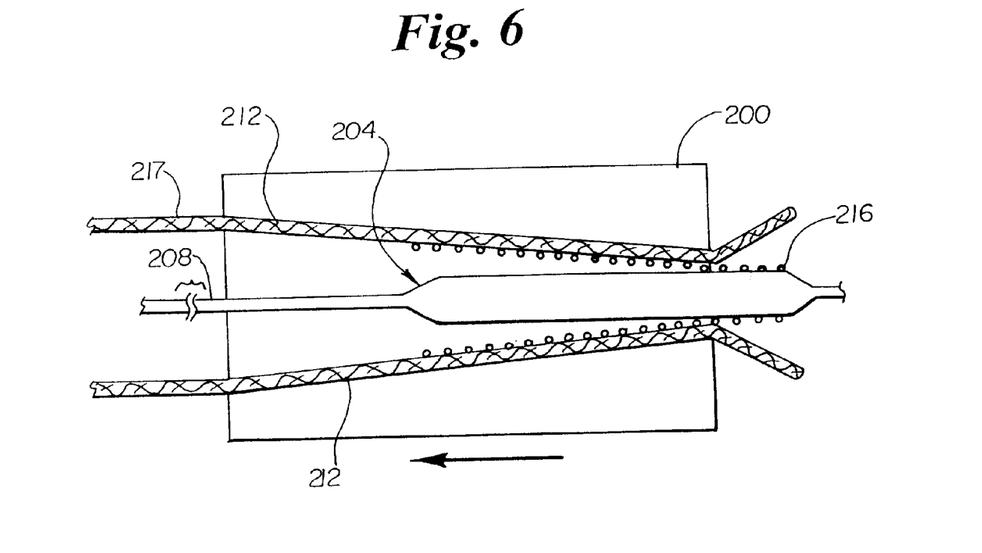
FIG. 6 shows a side view of another embodiment of the present invention.

FIG. 6 is a side view of a die 200, similar to those depicted in FIGS. 3–5, showing stent bearing region generally indicated at 204 of a catheter 208 as it traverses a bore 212. Stent 216 is compressed and crimped as it traverses bore 212 by movement of die 200 is indicated by the arrow. Extending through bore 212 is inner tubing 217.

Figure 7:
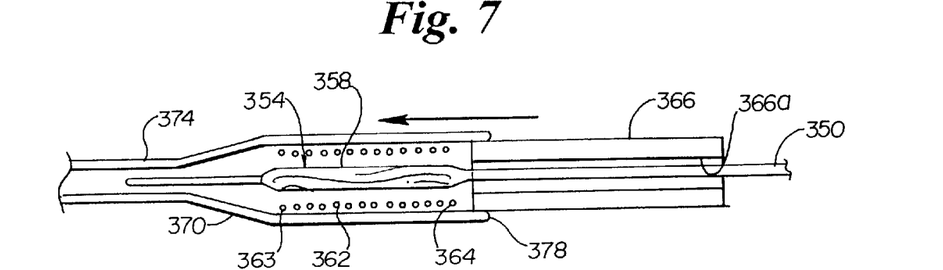
FIG. 7 shows a side view of another embodiment of the present invention.

In another embodiment, illustrated in FIG. 7, a catheter 350 having a stent bearing region generally indicated at 354, with a balloon 358 mounted thereon, and a stent 362, the stent having a first end 363 and a second end 364, is provided with a first peel away tube 366. First peel away tube 366, characterized by a predetermined inner diameter, 366a, is located adjacent to the second end 364 of stent 362 and serves as a stent retention means to prevent stent 362 from sliding along catheter 350 during crimping. A tapered peel away tube 370 having a first end 374 with a first diameter and a second end 378 with a second diameter, the second diameter being larger than the first diameter, surrounds a portion of catheter 350 at the first end 363 of the stent 362 when moved as indicated by the arrow. Tapered peel away tube 370 serves as a crimping means. The second diameter of tapered peel away tube 370 is larger than the diameter of uncrimped stent 362 while the first diameter of tapered peel away tube 370 is smaller than the diameter of the uncrimped stent. Optionally, the stent may rest in a sleeve (not shown) to prevent nicking or other damage to the stent. In use, tapered peel away tube 370 is slidably passed over stent 362 when moved as indicated by the arrow. As the tapered end of tapered peel away tube 370 passes over stent 362, the stent is crimped. Following crimping first peel away tube 366 and tapered peel away tube 370 may then be peeled away from catheter 350. Optionally, a two part sleeve which can be broken off may be used to crimp the stent in place of the tapered peel away tube.

Suitable materials for the first peel away tube and the tapered peel away tube include scored polyethylene, polypropylene and teflon. Preferably tapered peel away tube will 370 be made of a clear or translucent material. Tapered peel away tube 370 must be made of a material less deformable than the stent so that as it passes over the stent, the stent will be crimped rather than the tube being deformed. The first peel away tube 366 may be formed of any material rigid enough to prevent the stent from sliding.

In another embodiment, the present invention discloses a stent-crimping apparatus comprising a deformable tube and a tension applying means for applying tension to the deformable tube and a method of crimping a stent using the same. The stent bearing region of a catheter, along with a stent, is inserted into the deformable tube. As the tension applying means stretches the deformable tube, the diameter of the tube decreases, thereby crimping the stent onto the catheter.

Figure 8:
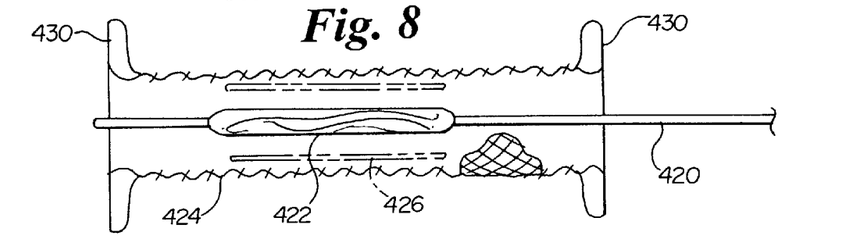
FIG. 8 shows a side view of another embodiment of the present invention.

As depicted in FIG. 8, a catheter 420 bearing a balloon 422 is inserted in a deformable tube 424. Stent 426 is separately inserted into deformable tube 424 so that it rests over at least a portion of balloon 422. Deformable tube 424 has grips 430 at each end. While grips 430 may be an integral part of deformable tube 424, they may also be adhesively or pressure bonded to deformable tube 424. Deformable tube 424 will preferable be formed of a braid, the characteristics of which have been discussed herein above. Grips 430 may be made of any material which facilitates holding onto the device., including plastics and metals. In operation, a stent 426 is aligned over balloon 422 and tension applied to both grips 430 so as to stretch deformable tube 424. As deformable tube 424 stretches, its diameter decreases, thereby applying an inward force to stent 426 and crimping it to balloon 422 and catheter 420.

Figure 9:
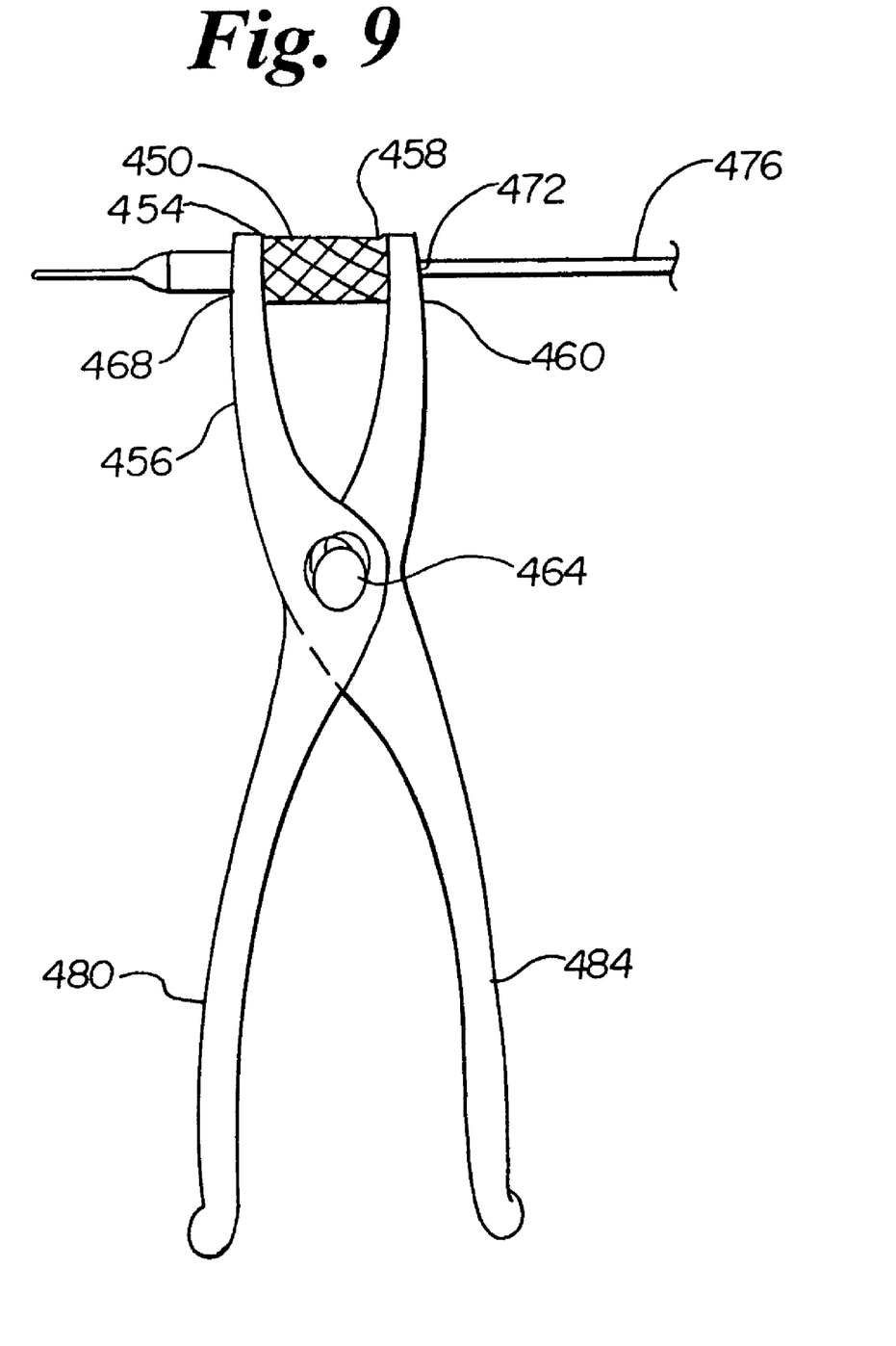
FIG. 9 shows a side view of another embodiment of the present invention.

The apparatus, shown in FIG. 9 illustrates an embodiment of the above invention. The apparatus comprises a deformable tube 450 fixed at a first end 454 to a first arm 456, and fixed at a second end 458 to a second arm 460. The two arms are pivotally connected at 464. The first and second arms have apertures 468 and 472 therethrough respectively. In use, a catheter 476 is inserted through the aperture 468 or 472, traversing the deformable tube 450 and exiting via the aperture 468 or 472 such that the stent bearing region of the catheter (not shown) resides in the deformable tube. A stent (not shown) is then inserted in deformable tube 450 so that it rests over the stent bearing region of the catheter. Optionally, a deformable sleeve (not shown) may be contained within the deformable tube as well. As arms 456 and 458 are squeezed together at 480 and 484, the arms exert a longitudinal tension on the deformable tube, stretching deformable tube 450 and decreasing the diameter of deformable tube 450 thereby crimping the stent to the stent bearing region of the catheter.

In another embodiment the present invention provides a method for crimping a crimpable stent onto a catheter, the catheter possessing a stent bearing region. The stent is characterized by a first diameter prior to crimping and a second, smaller diameter following crimping. The method comprises the steps of placing a stent coaxially on the stent bearing region of the catheter, and placing a stent retaining means such as a deformable tube over the stent, as discussed above. The deformable tube has a longitudinal axis, and a first diameter in the absence of tension and a second, smaller diameter when the tube is under tension along the longitudinal axis. Longitudinal tension is placed on the tube so as to fix the stent in place on the stent bearing region of the catheter and to substantially prevent relative motion between the tube and the stent. A stent crimping means such as a die containing a bore is provided, a portion of the bore with a diameter smaller than the first diameter of the stent. Relative sliding movement is then provided between the stent crimping means and the stent, with the stent crimping means traversing the stent bearing region of the catheter and thereby crimping the stent.

Figure 10A:
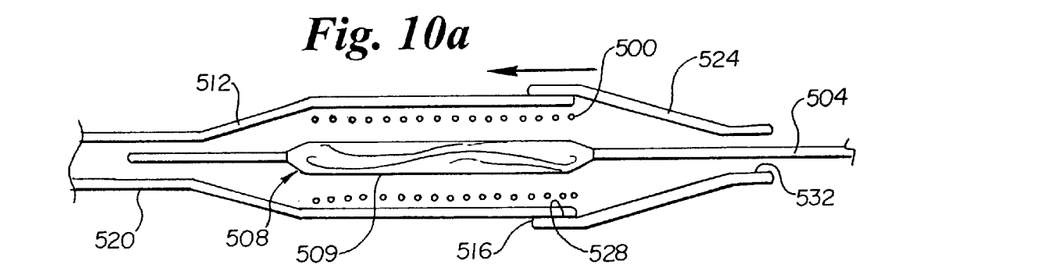
FIG. 10a shows a side view of another embodiment of the present invention.
Figure 10B:
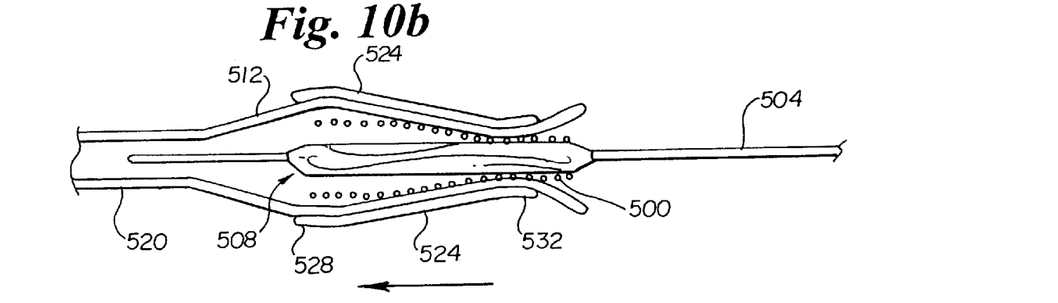
Figure 10C:
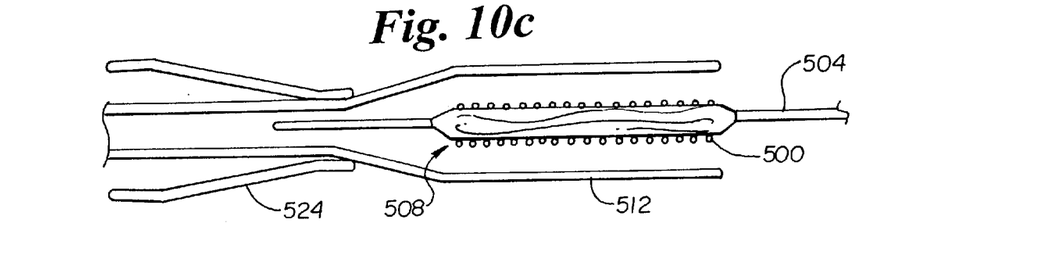

In another embodiment, illustrated by FIG. 10a, the present invention provides a method for affixing a stent 500 onto a catheter 504. A stent 500 is placed coaxially on stent bearing region generally indicated at 508 of catheter 504 including a balloon 509 and a stent retaining means such as a deformable, optional peel-away tube 512 is placed coaxially over stent bearing region 508 of catheter 504. While peel-away tube 512 is depicted as being tapered, it need not be tapered. Although allowably deformable, the stent retaining means should prevent sliding of stent 500. A crimping means such as a tapered tube 524 having a first opening 528 with a first diameter and a second opening 532 with a second diameter, the second diameter being smaller than the first diameter, is positioned coaxially over catheter 504. Although the interior of tapered tube 524 is tapered, the exterior may be tapered as well. As the crimping means (tapered tube 524) passes over stent 500 as indicated by the arrow, stent 500 is partially crimped onto catheter 504, as illustrated in FIG. 10b. After tapered tube 524 has completely passed over stent bearing region 508, as depicted in FIG. 10c, stent 500 is crimped to catheter. The crimping means (tapered tube 524) and deformable tube 512 may then be removed, optionally, by peeling them off. Suitable peel-away tube materials include scored polyethylene, polypropylene and teflon.

As in the first of the above-mentioned embodiments, the tubes may be made of a clear or translucent material so as to facilitate positioning of the stent and catheter within. Optionally, the tube may be made of a polymer braid or a metal braid such as nitinol and/or have a lubricious coating on the inner surface of the tube. The tube must be round on the inside although the exterior need not be round.

It is understood that in all of the embodiments of the present invention, whether explicitly stated or not, an optional protective tube surrounding the stent may be included to protect the stent from damage.

In those embodiments of the present invention in which a die is used, as in the first embodiment, the die may be made of metal or of a polymer. It is most desirable for the bore within the die to be tapered such that the tapered diameter is smaller than the initial diameter of the stent to be crimped.

In yet another embodiment of the present invention, the apparatus discussed above are prepared with an automated mechanism (not shown) to apply tension to the tube or slidably move the appropriate tubes or shafts. The automated mechanism may include a motor (not shown).

In yet another embodiment of the present invention, the apparatus comprises a tubular plunger in communication with one end of an inner tube. The plunger is slidably mounted in an outer tube. The inner tube, which receives the stent and catheter, traverses the inner bore of a slotted die. The other end of the inner tube is fixedly attached to an end portion. The outer tube serves as a sheath to protect the inner tube and preferably is slotted at one end. The slotted end of the outer tube is received by the slots in the die. In order to crimp the stent, the die is slidably moved over the stent residing in the inner tube. As the stent passes through the inner bore, at least a portion of the inner bore having a smaller diameter than that of the uncrimped stent, the stent is crimped down onto the catheter or onto a dilatation balloon mounted on the catheter.

Figure 11A:
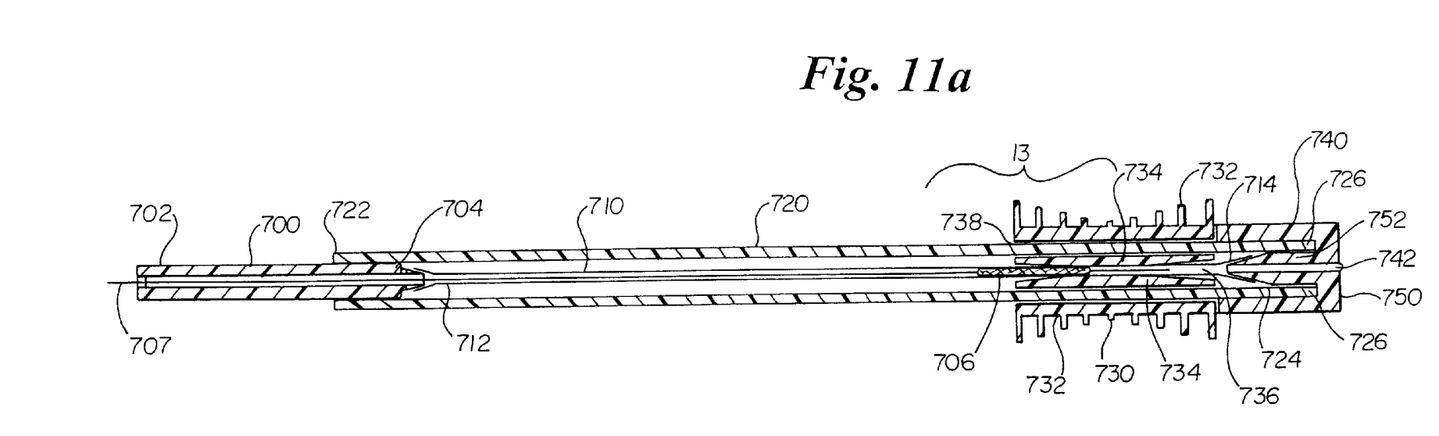
FIG. 11a is a side elevational view sectioned vertically along the longitudinal axis of yet another embodiment of the invention.
Figure 11B:
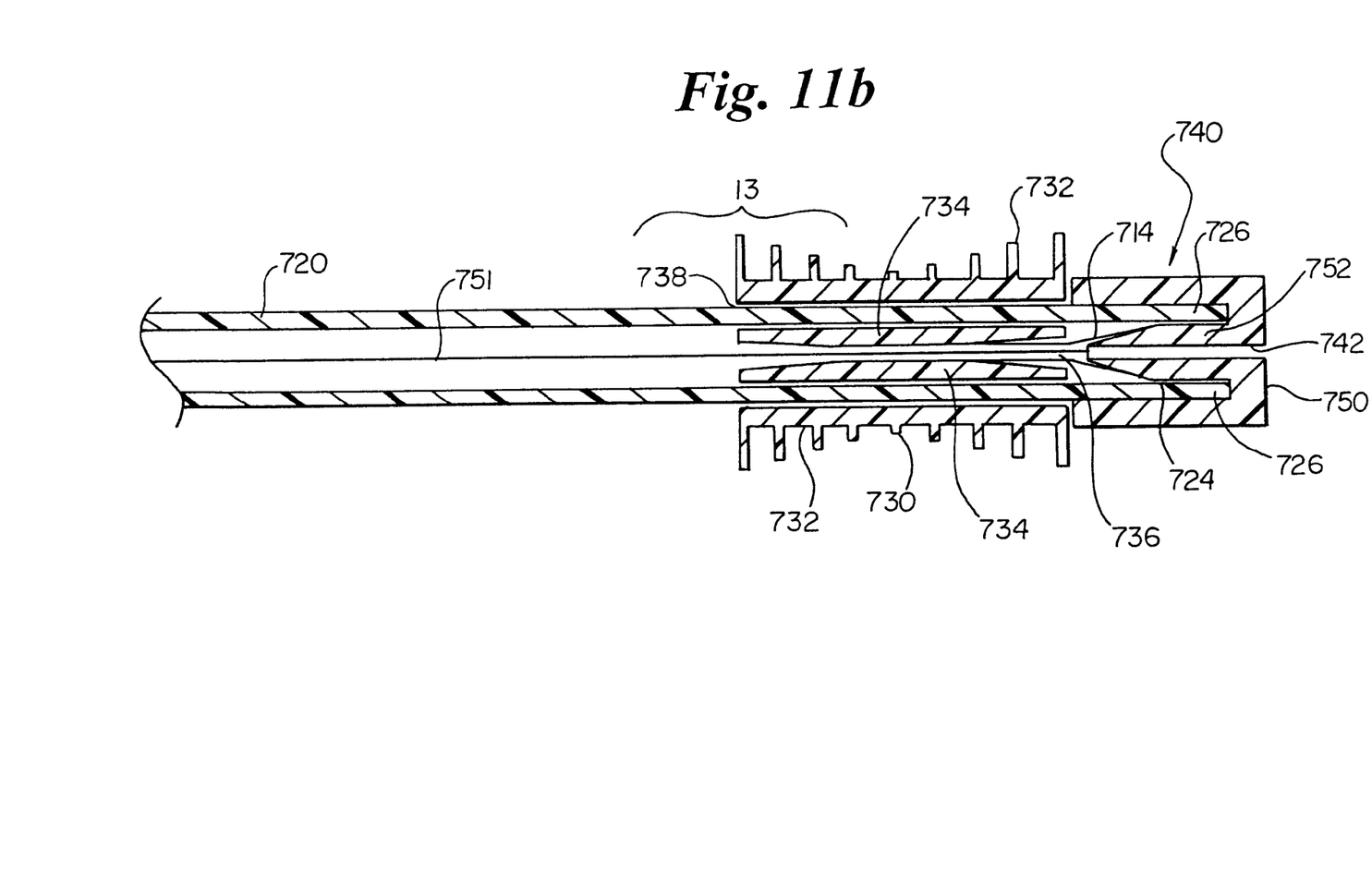
FIG. 11b shows the stent crimper of FIG. 11a absent the catheter and with an optional mandrel present.
Figure 12:
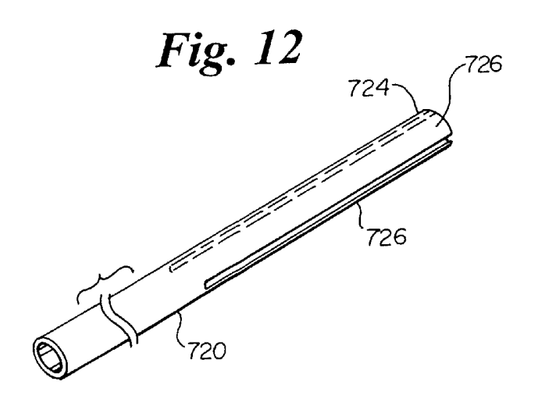
FIG. 12 is a detailed fragmentary view of the outer tube depicted in FIG. 11 showing the notched end of the outer tube.

This embodiment of the device is illustrated in FIG. 11. A tubular plunger 700 having a first end 702 and a second end 704 and characterized by an inner diameter exceeding the diameter of the uncrimped stent is attached to and in communication with a deformable inner tube 710. Inner tube 710 receives stent 706 and catheter 707 through plunger 700, and is fixedly attached to the second end of the tubular plunger 704 by pressing, or the use of adhesives. Deformable inner tube 710 has a first end 712 and a second end 714. The device further comprises an outer tube 720 having a first end 722, and a second end 724. As depicted in FIG. 12, outer tube 720 is notched at second end 724 so as to have a plurality of (two) oppositely situated wall sections 726 at the second end. The second end of the plunger 704 is slidably mounted in the first end 722 of the outer tube 720 and deformable inner tube 710 resides within outer tube 720. A die 730 (depicted in FIGS. 11a, b, 13 and 14) is slidably mounted on outer tube 720. Die 730 has an outer housing 732 and an inner housing 734 with an inner bore 736 therethrough, inner bore 736 having a circular cross-section at every point along the length of the inner bore. Inner bore 736 is characterized by a minimum diameter, with the diameter of stent 706 prior to crimping exceeding the minimum diameter of the bore. A portion of inner tube 710 traverses inner bore 736. Die 730 further has one or more slots 738 therethrough arranged so as to receive the plurality of oppositely situated wall sections 726 in sliding engagement. Finally, the device has an end portion shown generally at 740 at the second end of outer tube 720. Optionally, end portion 740 has a hole 742 therein from which catheter 707 may emanate. Finally, reverting to FIG. 11, end portion 740 may comprise a cap 750 mounted on the second end of the outer tube. Cap 750 comprises a male part 752 extending inward to which second end 714 of inner tube 710 is fixedly attached, either by bonding, pressing or some other suitable method so that the inner tube may be placed under pressure by pulling on the plunger. Cap 750, prevents die 730 from sliding off of outer tube 720. Cap 750, like the outer tube, may be made of rigid materials including polymers and metals. End cap 750 may be a separate piece or may be molded as an integral part of outer tube 720. End cap 750 optionally has a hole within allowing for the insertion or removal of the catheter from the inner tube.

Optionally, the device may further comprise a mandril 751 as shown in FIG. 11 b. In one embodiment, the mandril may emanate from end cap 750 and traversing inner tube 710 and plunger 700. Mandril 751 may serve as a guide for inserting the catheter and stent.

The plunger 700 may be made of any rigid material. Preferably, it will be made of a clear material such as a polycarbonate. However, other polymers or metals including stainless steel may be used as well. As depicted in FIG. 11, the second end 704 of plunger 700 is tapered. While not a necessary feature of the invention, the taper allows for ease of mounting inner tube 710 on plunger 700. The first end of plunger 700 is chamfered to facilitate receipt of the stent therein, although the chamfering is not necessary to the device.

The deformable inner tube 710 may be made of any deformable material softer than the stent. The tube must be susceptible to deforming in such a way that at least a portion of the tube exhibits a reduced diameter upon stretching of the tube. While the interior of the tube must have a circular cross section, the exterior of the tube, while preferably having a circular cross-section, need not have a circular cross section. The tube may be a sheath formed from Teflon, polyethylene, polypropylene or any other material softer than the stent. The tube may also consist of a braid of constant pic count, preferably ranging from about 30 to about 90, most preferably about 40. While a flat ribbon braid which is tubular on the inside may be used, preferably a round braid will be used. Suitable materials for a braid include polyimide or polyester and nylon as well as metals such as Nitinol. Suitable braid tubes are manufactured by SCIMED Life Systems, Maple Grove, Minn., SantaFe Textiles, Inc., Los Angeles, Calif., or any other coil braider. It is preferable that the tube be formed of a clear or translucent material for ease of positioning the stent. Optionally, there can be a step down in the inner tube diameter between the first opening and the second opening of the tube. The step down serves as a stop for ease of positioning the stent. The diameter of the unstretched tube at the first end may exceed the diameter of the uncrimped stent. The tube may be coated with either a lubricity enhancing coating or a coating to enhance holding forces on the outside or inside. To facilitate positioning the stent relative to the catheter, the tube may be marked with position markers and may further be made of a magnifying material to facilitate visualizing the stent and catheter.

As in the previous embodiments, the deformable inner tube 710 serves not only to protect the stent from damage such as nicking, but also serves to hold the stent in place during crimping and prevent elongation of the stent.

The deformable inner tube 710 may be attached to plunger 700 by any known means including adhesive bonding and press fitting (i.e. frictionally bonding).

The outer tube 720, like the plunger, may be made of any rigid material. Preferably, however, the outer will be made of a clear or translucent material to enable the stent to be seen as it is positioned. Optionally, outer tube 720 may further comprise a magnifying window (not shown) so as to facilitate positioning stent 706. The magnifying window may be made of any magnifying materials. The outer tube 720 may also be illuminated (not shown) to facilitate viewing the stent. In operation, the outer tube 720 helps to contain the deformable inner tube 710 and prevent it from protruding when the plunger is depressed. The plunger is depressed while the stent is loaded. The outer tube further serves as a protective packaging where the stent is prepackaged in the stent crimping device. The walls of inner tube 710 may also be coated with a lubricious coating to facilitate sliding the die over it.

The die 730 may be made of any material harder than the stent, including metals and polymers such as polycarbonate. Other suitable materials include acetals, such as delrin, or lubricious materials such as polyethylene and nylon. One embodiment of the die, shown in FIG. 13 comprises an outer housing 732 and an inner housing 734 in communication with one another, slots 738 between the inner housing and the outer housing and an inner bore 736, traversing inner housing 734. Although die 730 is depicted with baffles 739 thereon, any ergonomic design to the outer housing may be used.

The diameter of the stent prior to crimping exceeds the minimum diameter of the bore. Where the diameter of the bore is constant along the length of the bore, the maximum and minimum diameters are equivalent. Preferably, the bore will be tapered from one or both sides of the die. In the former case, the bore tapers from a maximum diameter at the first end of the die to the minimum diameter at the second end of the die. In the latter case, as depicted in FIG. 11, the diameter of the bore decreases along the length of the bore until a region of minimum diameter is encountered. Following the region of minimum diameter, the diameter of the bore increases along the remaining length of the bore. The region of minimum diameter may constitute a single point along the length of the bore or may extend for a desired length. The taper need not be symmetric. Thus, the taper of the bore on the first end can extend over a greater or lesser length than the taper on the second end. Finally, although die 730 is depicted with baffles 739 on the exterior, any ergonomic design for the exterior of the baffle may be used.

Figure 15:
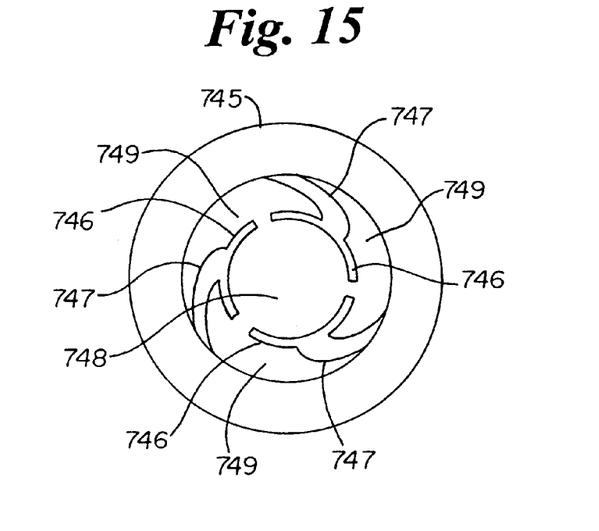
FIG. 15 is a detailed sectional view of another embodiment of a die.
Figure 16A:
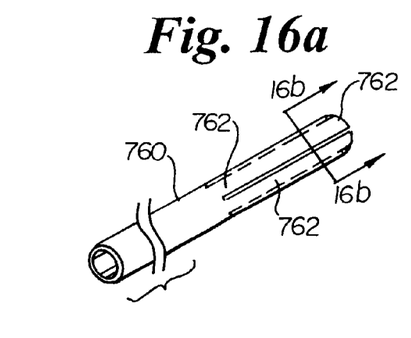
FIG. 16a is a detailed perspective view of an outer tube used with the die of FIG. 15.
Figure 16B:
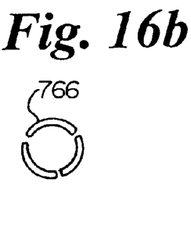
FIG. 16b is a detailed cross sectional view of the outer tube of FIG. 16a taken along line 16b—16b.

In another embodiment of the die, as depicted in FIG. 15, the die comprises an outer housing 745 and an inner housing defined by inner housing members 746. Inner housing members 746 are attached to the outer housing via posts 747. Preferably, posts 747 are made of a springy material, including stainless steel and nitinol, allowing the diameter of the substantially circular inner bore 748 to be varied. Slots 749 lie between outer housing 745 and the inner housing members 746. In operation, such a die allows for the crimping of a variety of stents with different diameters to balloons of differing diameters. As the stent and balloon enter the die, inner housing members 746 retracts until the spring force is sufficient to begin crimping the stent. This will occur when the compression is such that the spring force exceeds the maximum force to which the stent can be subjected without deforming. The use of the springy material ensures the application of a consistent crimp retention force over a variety of stent and balloon diameters. Of course, the outer tube must be slotted so as to cooperate with the slots 749. One such tube is shown generally at 760 in FIG. 16a. The tube has three side walls 762. A sectional view of the slotted end is shown at 766 in FIG. 16b.

Figure 17:
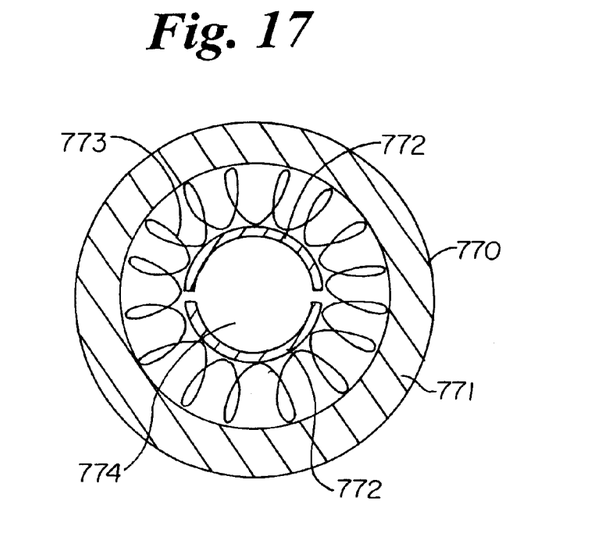
FIG. 17 is a detailed cross sectional view of another die useful in the invention.

In another embodiment of the die, as depicted in FIG. 17, die generally indicated at 770 comprises a tubular outer housing 771 and two spaced half-tubular inner housing elements 772. Coil springs 773 line the space between tubular outer housing 771 and half-tubular inner housing elements 772. Half-tubular inner housing elements 772 define a bore 774 for receiving the stent and catheter (not depicted) with a substantially circular cross-section. Although springs 773 are not directed radially inward, the invention also contemplates the use of springs oriented radially inward. Tubular outer housing 771 as well as half-tubular inner housing elements 772 may be made of the same materials as those used for other embodiments of the die such as stainless steel and polymers such as polycarbonate, acrylonitrile-butadiene-styrene copolymer, Nylon, acetal, and PEEK (polyetheretherketone). As the catheter and stent (preferably in an inner tube) with a diameter exceeding the diameter of inner bore 774 are inserted into bore 774, springs 773 compress. When springs 773 are sufficiently compressed that the force exerted by the springs exceeds the maximum force to which the stent may be subjected without deformation, the stent will compress. For a given choice of spring with given spring constant, this design allows for a variable crimp depending on the physical properties of the stent being crimped. Stents made of materials less susceptible to deformation will not be crimped to the same extent as stents more susceptible to deformation. This is in marked contrast to those die embodiments which do not use springs. Absent the springs, all stents passing through the die will be crimped to a diameter equal to the minimum diameter of the inner bore.

Figure 13:
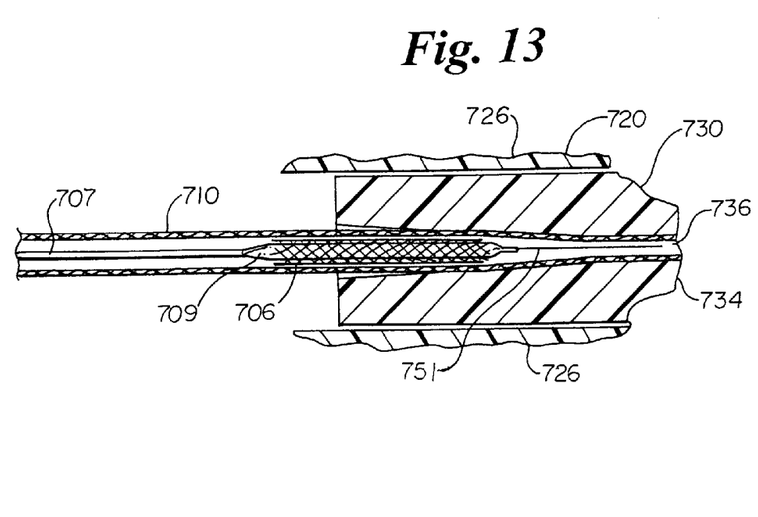
FIG. 13 is an enlarged fragmentary section taken from the area bracketed by 13 in FIG. 11 showing the die of FIG. 11 in detail.
Figure 14:
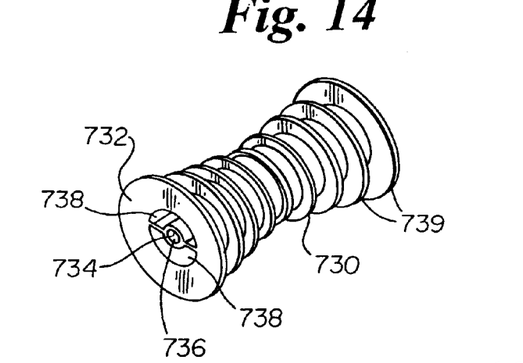
FIG. 14 is a detailed perspective view of the die depicted in FIG. 11.

In operation, stent 706 is crimped to the balloon and catheter as depicted in FIG. 13 by inserting stent 706 and catheter 707 through the plunger and into inner tube 710, positioning stent 707 over stent bearing region 709 and sliding die 730 along outer tube 726 such that die 730 passes over stent 706 and applies a uniform radial inward force to the stent. Preferably, when the stent is inserted, the inner tube should be placed under sufficient tension that its diameter is approximately equally to that of the uncrimped stent. The stent may then be positioned relative to the catheter by tilting the device downward and depressing the plunger. In so doing, the diameter of the inner tube increases and, acting under gravity, the stent slides down in the inner tube until it reaches the desired location at which time the plunger may be pulled outward to apply tension to the inner tube thereby reducing the diameter of the inner tube and causing the inner tube to grip the stent and hold it in place as the die passes over the stent. If the stent goes too far in the inner tube, the process may be repeated, tilting the device in the opposite direction although such a step is not necessary if a step down braid or tube is included. Of course, the position of the catheter may also be adjusted by sliding the catheter relative to the stent.

The device may further comprise a ratcheting mechanism (not depicted) or a locking mechanism to control the amount of tension applied to the inner tube and lock the plunger into the package place when a desired tension has been placed on the inner tube. Such a mechanism would facilitate operation of the device by eliminating the need to pull on the plunger as the die is moved and the stent is crimped.

Figure 18:
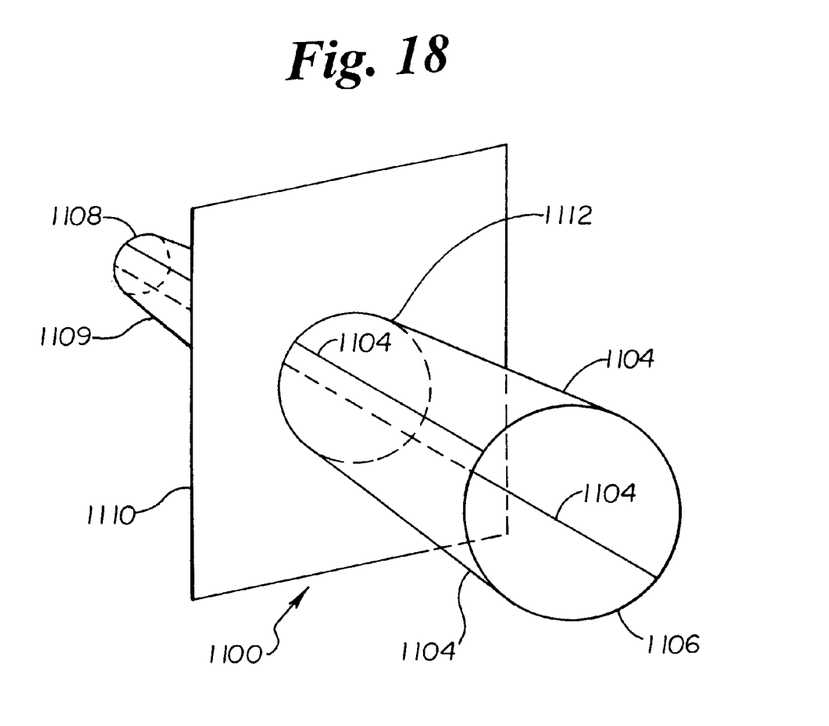
FIG. 18 is a perspective schematic showing of yet another embodiment of the invention.

In yet another embodiment, as depicted in FIG. 18, the stent crimping device shown generally at 1100 comprises an array of longitudinal wires 1104 formed of a metal such as stainless steel connected at one end with circular wire 1106 and at the other with circular wire 1108, the wires arranged in a frustoconical assembly 1109. Surrounding the wires is a die 1110 with a circular bore 1112 therethrough. The diameter of the circle defined by circular wire 1106 exceeds that of the uncrimped stent while the diameter of the bore 1112 is the desired diameter of the crimped stent. As can be seen from the figure, the diameter of the circle formed by circular wire 1108 is less than the diameter of the circle formed by circular wire 1106.

In operation, a stent (not shown) is placed on a stent bearing region of a catheter (not shown) and inserted through circular wire 1106 and into the frustoconical assembly. Die 1110 is slidably moved toward circular wire 1106 drawing longitudinal wires 1104 inward on the stent and thereby crimping the stent.

Although the device depicted in FIG. 18 is shown as being formed from four longitudinal wires as many as twelve longitudinal wires or more may be used in making the frustoconical device.

The die 1110 may be made of any material stronger than the stent and longitudinal wires to ensure that the stent is crimped rather than die being deformed. Stainless steel is one such material.

Common to all of the various embodiments disclosed above is the application of a uniform force to a compressible tube which, in turn, transmits the force to the stent and thereby crimps it uniformly on the catheter. The uniform force is applied in the various embodiments in one of two ways: first, by sliding the tube and its contents through a bore, preferably tapered so that as the tube traverses the bore, the bore exerts a uniform force on a circular cross section of the tube and second by elongating the tube resulting in a uniform reduction of the diameter along the tube. The bore may be the bore in a metal or polymer die or, alternatively, the bore in a tube or sheath, the tube or sheath optionally being tapered on the outside or the inside.

The crimping devices of the present invention may be prepackaged with a stent contained therein for single use, a stent and a catheter with an expandable region, or a stent, balloon and catheter. Alternatively, the crimping devices of the present invention may be used in conjunction with a stent prepackaged in a deformable tube which may be inserted into the crimping device along with the stent.

While this invention may be embodied in many different forms, there are described in detail herein specific preferred embodiments of the invention. This description is an exemplification of the principles of the invention and is not intended to limit the invention to the particular embodiments illustrated.

The above examples and disclosures are intended to be illustrative and not exhaustive. These examples and descriptions will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. An apparatus for compressing a stent onto a catheter, the stent having a first end and a second end and a diameter, the apparatus comprising a
    retaining means for maintaining the position of the stent on the catheter;
    a die for applying a uniform radial inward force to at least a portion of the stent, the die having a bore, the bore having a first end and a second end, the first end of the bore having a diameter larger than the diameter of the stent, the second end of the bore having a diameter smaller than the diameter of the stent; and
    a mounting apparatus comprising a rail upon which the die is slidably mounted.

2. The apparatus of claim 1 wherein the mounting apparatus comprises a catheter retaining means to prevent the catheter from moving.

3. An apparatus for compressing a stent onto a catheter, the stent having a first end and a second end and a diameter, the apparatus comprising a
    retaining means for maintaining the position of the stent on the catheter;
    a die for applying a uniform radial inward force to at least a portion of the stent, the die having a bore, the bore having a first end and a second end, the first end of the bore having a diameter larger than the diameter of the stent, the second end of the bore having a diameter smaller than the diameter of the stent; and
    a mounting apparatus comprising at least one rod upon which the die is slidably mounted.

4. The apparatus of claim 3 wherein the die comprises a transparent or translucent material.

5. The apparatus of claim 3 wherein the die has an interior surface, the interior surface being lubricious.

6. The apparatus of claim 3 further comprising a stent and a catheter.

7. The apparatus of claim 6 further comprising a balloon mounted coaxially at least partially underneath the stent.

8. The apparatus of claim 3 wherein the die moves longitudinally with respect to the stent.

9. A device for crimping a stent to a catheter, the stent having a diameter prior to crimping, comprising:
    a tubular plunger having a first end and a second end, the plunger having an inner diameter exceeding the diameter of the stent prior to crimping;
    a deformable inner tube for receiving the stent and catheter from the plunger, the inner tube fixedly attached to the second end of the tubular plunger, the deformable inner tube having a first end and a second end;

an outer tube, the outer tube having a first and a second end, the outer tube notched at the second end so as to have a plurality of oppositely situated wall sections at the second end, the second end of the plunger slidably mounted in the first end of the outer tube and the deformable inner tube residing within the outer tube;

a die slidably mounted on the outer tube, the die comprising an outer housing and an inner housing, the outer housing in communication with the inner housing, the inner housing having an inner bore therethrough, the inner bore having a circular cross-section at every point along the length of the inner bore, the bore characterized by a minimum diameter, the diameter of the stent prior to crimping exceeding the minimum diameter of the bore, a portion of the inner tube traversing the bore, the die further having one or more slots therethrough between the inner housing and the outer housing, the slots arranged so as to receive the plurality of oppositely situated wall sections in sliding engagement; and an end portion, the end portion residing at the second end of the outer tube, the end portion optionally having a hole therein from which the catheter may emanate; whereby the stent is crimped to the catheter by inserting the stent and catheter through the plunger and into the inner tube, and sliding the die along the outer tube such that the die passes over the stent and applies a uniform radial inward force to the stent.

10. The device of claim 9 wherein the inner tube is a braid.

11. The device of claim 10 further comprising a stent, the stent residing in the flexible inner tube.

12. The device of claim 9 wherein the inner tube is made of a clear or translucent material and the outer tube is made of a clear or translucent material.

13. The device of claim 9 wherein the inner tube is attached to the end portion.

14. The device of claim 9 wherein the end portion comprises a cap mounted on the second end of the outer tube.

15. The device of claim 9 wherein the outer tube is closed at the second end so as to form the end portion.

16. The device of claim 9 wherein the one or more portions of the inner bore are tapered.

17. The device of claim 9 wherein the diameter of the inner tube is stepped, the step serving as a stopper for the stent.

18. The device of claim 9 further comprising a mandril emanating from the end portion and coaxial with the inner tube, at least a portion of the mandril residing in the inner tube.

19. The device of claim 9 wherein the second end of the outer tube comprises two oppositely situated wall sections and the die has two slots therethrough to accommodate the wall sections.

20. The device of claim 9 wherein the second end of the outer tube comprises three oppositely situated wall sections and the die has three slots therethrough to accommodate the wall sections.

21. A method of crimping a stent onto a catheter, the catheter having a balloon mounted thereon, by:
 a) inserting the stent and catheter into the device of claim 9;
 b) aligning the stent over the balloon by moving the stent, the catheter or both;
 c) slidably moving the die over the stent so as to apply an inward radial force to at least a portion to the stent while preventing the stent from sliding by applying tension to the inner tube by pulling on the plunger; and
 d) removing the catheter from the device.

* * * * *

UNITED STATES PATENT AND TRADEMARK OFFICE
CERTIFICATE OF CORRECTION

PATENT NO. : 5,992,000

DATED : November 30, 1999

INVENTOR(S) : Humphrey et al.

It is certified that error appears in the above-identified patent and that said Letters Patent is hereby corrected as shown below:

Col. 7, line 11, Please delete the word "die," after the number 192;

Signed and Sealed this

Twentieth Day of March, 2001

*Attest:*

*Attesting Officer*

NICHOLAS P. GODICI

Acting Director of the United States Patent and Trademark Office